US006805711B2

(12) United States Patent
Quijano et al.

(10) Patent No.: US 6,805,711 B2
(45) Date of Patent: Oct. 19, 2004

(54) EXPANDABLE MEDICAL IMPLANT AND PERCUTANEOUS DELIVERY

(75) Inventors: Rodolfo C Quijano, Laguna Hills, CA (US); Hosheng Tu, Newport Beach, CA (US)

(73) Assignee: 3f Therapeutics, Inc., Lake Forest, CA (US)

( * ) Notice: Subject to any disclaimer, the term of this patent is extended or adjusted under 35 U.S.C. 154(b) by 0 days.

(21) Appl. No.: 10/173,188

(22) Filed: Jun. 17, 2002

(65) Prior Publication Data

US 2003/0191528 A1 Oct. 9, 2003

Related U.S. Application Data

(63) Continuation-in-part of application No. 09/627,523, filed on Jul. 28, 2000, now Pat. No. 6,406,493, which is a continuation-in-part of application No. 09/587,135, filed on Jun. 2, 2000, now abandoned.

(51) Int. Cl.[7] .................................................. A61F 2/24
(52) U.S. Cl. .................................... 623/2.37; 623/2.38
(58) Field of Search .............................. 623/2.37, 2.36, 623/900, 2.14, 2.17, 2.18, 1.24, 2.19, 1.36, 2.38

(56) References Cited

U.S. PATENT DOCUMENTS

| | | | | | |
|---|---|---|---|---|---|
| 4,491,986 | A | | 1/1985 | Gabbay | |
| 5,061,277 | A | | 10/1991 | Carpentier et al. | |
| 5,104,407 | A | | 4/1992 | Lam et al. | |
| 5,163,952 | A | | 11/1992 | Froix | |
| 5,163,953 | A | * | 11/1992 | Vince | 623/2 |
| 5,593,435 | A | | 1/1997 | Carpentier et al. | |
| 5,840,081 | A | | 11/1998 | Andersen et al. | |
| 5,855,601 | A | * | 1/1999 | Bessler et al. | 623/2 |
| 5,888,240 | A | | 3/1999 | Carpentier et al. | |
| 6,033,433 | A | | 3/2000 | Ehr et al. | |
| 6,042,606 | A | | 3/2000 | Frantzen | |
| 6,077,298 | A | | 6/2000 | Tu et al. | |
| 6,224,625 | B1 | | 5/2001 | Jayaraman | |
| 6,283,127 | B1 | | 9/2001 | Sterman et al. | |
| 6,458,153 | B1 | * | 10/2002 | Bailey et al. | 623/1.24 |
| 6,602,289 | B1 | * | 8/2003 | Colvin et al. | 623/2.37 |
| 2002/0032481 | A1 | * | 3/2002 | Gabbay | 623/2.11 |

OTHER PUBLICATIONS

Georg Lutler et al. "Percutaneous Aortic Valve Replacement: An Experiment Study, I. Studies on Implantation" J Thorac Cardiovasc Surg 2002; 123: 768–776.

Younes Boudjemline et al., "Steps Toward Percutaneous Aortic Valve Replacement" Circulation 2002;105: 775–778.

* cited by examiner

*Primary Examiner*—Bruce Snow
(74) *Attorney, Agent, or Firm*—Jones Day

(57) ABSTRACT

An expandable annular ring for implantation in a valvular annulus and its percutaneous use thereof comprises a plurality of stenting elements made of a first shape-memory material having a first shape-transition temperature, wherein the first shape-memory material expands to a preshape when the first shape-memory material is heated to above the first shape-transition temperature; and a plurality of anchoring elements made of a second shape-memory material having a second shape-transition temperature that is higher than the first shape-transition temperature, wherein the second shape-memory material expands to the second preshape when the second shape-memory material is heated to above the second shape-transition temperature.

20 Claims, 11 Drawing Sheets

17 11 13 16 51E 12 44 51F 11 51G 51H 17 11 13 16 52 12 44 11 53

51G
51F
12
51E
51H
11
13
44
11
17
16

EXPANDABLE MEDICAL IMPLANT AND PERCUTANEOUS DELIVERY

RELATIONSHIP TO COPENDING APPLICATION

This patent application is a continuation-in-part application of Ser. No. 09/627,523 filed Jul. 28, 2000, now U.S. Pat. No. 6,406,493, which is a continuation-in-part application of Ser. No. 09/587,135 filed Jun. 2, 2000, now abandoned; the entire contents of which are incorporated herein by reference.

FIELD OF THE INVENTION

The present invention generally relates to improved medical devices and their use. More particularly, the present invention relates to a medical implant having an annular ring and its percutaneous delivery means that is expandable for correction of certain disorders in the heart valves, blood vessel valves or other valvular body conduits in a patient.

BACKGROUND OF THE INVENTION

The human's circulatory system consists of a heart and many blood vessels. In its path through the heart, the blood encounters four valves. The valve on the right side that separates a right atrium from a right ventricle has three cusps and is called the tricuspid valve. It closes when the ventricle contracts during a phase known as systole and it opens when the ventricle relaxes, a phase known as diastole. The pulmonary valve separates the right ventricle from a pulmonary artery. The mitral valve, so named because of its resemblance to a bishop's mitre, is in the left ventricle and it separates the left atrium from the ventricle. The fourth valve is the aortic valve that separates the left ventricle from the aorta. In a venous circulatory system, a venous valve is to prevent the venous blood from leaking back into the upstream side so that the venous blood can return to the heart and consequently the lungs for blood oxygenating and waste removing purposes.

In many patients who suffer from diseased or congenitally dysfunctional cardiovascular tissues, a medical implant may be used to correct the problems. A dysfunctional heart valve hinders the normal functioning of the atrioventricular orifices and operation of the heart. More specifically, defects such as narrowing of the valve stenosis or a defective closing of a valve, referred to as valvular insufficiency, result in accumulation of blood in a heart cavity or regurgitation of blood past the valve. If uncorrected, prolonged valvular insufficiency may cause eventually total valve replacement. On the other hand, certain diseases cause the dilation of the heat valve annulus. Dilation may also cause deformation of the valve geometry or shape displacing one or more of the valve cusps from the center of the valve. Dilation and/or deformation result in an ineffective closure of the valve during ventricular contraction, which results in regurgitation or leakage of blood during contraction.

It is known to use annuloplasty ring in the repair of diseased or damaged atrioventricular valves that do not require replacement. The annuloplasty ring is designed to support the functional changes that occur during the cardiac cycle: maintaining coaptation and valve integrity in systole while permitting good hemodynamics in diastole. The annuloplasty ring also provides support for the mitral or tricuspid annulus and restricts expansion of the annulus or portions of the annulus to preset limits.

A variety of annuloplasty rings have been employed, ranging from rigid rings of fixed sizes to flexible rings with a degree of adjustability. Obviously, annular prostheses that are of rigid fixed size must be carefully selected and skillfully sutured in place. Thus, an imperfect fit may require corrective surgery to replace the improperly implanted prosthesis. A rigid ring also prevents the normal flexibility of the valve annulus and has a tendency of sutures tearing during the normal movement of the valve annulus. Examples of rigid or partially rigid annuloplasty rings are disclosed in U.S. Pat. No. 5,061,277 (to Carpentier et al.) and in U.S. Pat. No. 5,104,407 (to Lam et al.).

Over the years flexible annuloplasty rings are designed and developed to overcome the problems of rigid rings and/or fixed size. One problem associated with the fixed size annuloplasty rings of the prior art is that, when such annuloplasty rings are implanted into children, the subsequent growth of the patient may render the annuloplasty ring too small for its intended function. Thus, a follow-up surgery may be necessary to replace the originally implanted annuloplasty ring with a larger ring suitable for the then-current size of the patient.

Another disadvantage of a fixed size, rigid annuloplasty ring is its bulkiness that requires an open-heart surgery for implantation. It is desirable to devise a retractable/expandable annuloplasty ring or annular ring having uni-flow means for allowing one-direction flow that is implantable via a minimally invasive manner, such as percutaneous procedures. Percutaneous aortic valve replacement reduces surgical trauma and hospital stay. For example, Boudjemline et al. (Circulation 2002;105:775–778) reports "steps toward percutaneous aortic valve replacement" and Lutter et al. (J Thorac Cardiovasc Surg 2002;123:768–76) reports "Percutaneous aortic valve replacement: An experimental study". It is one aspect of the present invention to provide an expandable annular ring with a uni-flow mechanism that has tissue-anchoring capability.

Carpentier et al., in U.S. Pat. No. 5,593,435 and No. 5,888,240 describes an annuloplasty ring which is constructed and equipped for post-implantation size adjustment in situ to accommodate changes in annular size due to growth of the patient. It is disclosed that a distensible annuloplasty ring may be made up of a plurality of separate segments which are slidably or movably secured to one another to form a ring. It is also disclosed that when dilatory or outward pressure is exerted against the inner surface of the ring, as may be accomplished by way of a radially expandable balloon introduced within the annulus of the remodeled valve, such pressure will cause the segments to slide or distend relative to one another. However, such mechanical sliding or distension of the segments expands the circumference of the ring by an incremental increase at only a few joint points where any two slidable segments meet. By distending an incremental strain and simultaneously loading most of the distension stress at a few joint points, the overall shape of the annulus may be distorted. Furthermore, the intended valve functionality with that unevenly distended annuloplasty ring after a period of tissue ingrowths into and/or encapsulation onto the annuloplasty ring may be compromised.

The disadvantages of the above-cited patents restrict the medical implants from retractable/expandable capability tailoring for percutaneous insertion by a minimally invasive manner.

Cardiovascular stents have been developed and used widely. A stent is a generally longitudinal tubular mesh-like device formed of biocompatible material, preferably a metallic or a plastic material, which is useful in the treatment of stenosis, strictures or aneurysms in body conduits such as blood vessels or around a valvular annulus. When a stent is expanded and enlarged, the whole section is expanded at essentially the same degree of extension. Special features of the stent configuration may include radially expandable non-axial contraction and/or spirals as disclosed in U.S. Pat. No. 6,042,606 (to Frantzen) and No. 6,033,433 (to Ehr et al.).

Balloon-assisted radial expansion for an expandable annuloplasty ring might restrict the blood flow undesirably. Radial mechanical force as disclosed in the prior art to expand an annuloplasty ring at a later time might not evenly expand the ring radially.

Shape-memory material has been disclosed and widely used that it will return to its preshape when it is activated by energy or other suitable means. The shape-memory material may include plastic material, metal, and the like. For example, U.S. Pat. No. 5,163,952 (to Froix) discloses shape-memory plastic. The entire contents of these patents are incorporated herein by reference.

Particularly, U.S. Pat. No. 6,077,298 issued to one co-inventor of the present invention, contents of which are incorporated herein by reference in its entirety, discloses a retractable/expandable stent and methods thereof using shape-memory metallic material.

Therefore, it would be desirable to provide an expandable annular ring, preferably with a uni-flow means configured for allowing one-directional flow that has uniformly distending properties circumferentially to conform to the natural valve annulus of the patient without suffering the above-discussed disadvantages of localized stress at only a few joint points where any two slidable segments meet. The improved annular ring may be preferably evenly expanded by non-mechanical means, such as shape-memory mechanisms and is implantable via a minimally invasive manner, such as percutaneous procedures at its retracted state.

SUMMARY OF THE INVENTION

In general, it is an object of the present invention to provide an expandable annular ring which may be radially expanded in situ by way of non-mechanical expandable means. It is another object of the present invention to provide an expandable annular ring with essentially uniform ring distension in the circumferential direction for at least one expansion process. It is still another object of the present invention to provide a method for expanding the radially expandable annular ring so that the annular ring is in a retracted state sized for percutaneous insertion and delivery through an intercostal opening or an incision on a blood vessel. It is a further object of the present invention to provide expanding means including heating or cooling the annular ring made of shape-memory material.

It is another aspect of the present invention to provide an expandable annular ring having a uni-flow mechanism configured to allow fluid to flow through the annular ring in only one direction. In one embodiment, the uni-flow mechanism is a check valve that allows fluid to flow in one direction, but not in an opposite direction. In another embodiment, a natural heart valve or venous valve having valvular cusps is one kind of the uni-flow mechanisms referred herein.

In accordance with one embodiment of the invention, the annular ring may comprise a fabric sheath, and at least one stenting element mounted within the fabric sheath, wherein the at least one stenting element is made of shape-memory material. The shape-memory material has a preshape and a shape-transition temperature, wherein the shape-memory material expands to its preshape so as to expand the annular ring when the shape-memory material is heated above or cooled to below the shape-transition temperature. In one embodiment, the annular ring so formed is a completely close ring while in an alternative embodiment, the annular ring is an open ring. The annular ring has the desired configuration of the mitral or tricuspid valve annulus. In one preferred embodiment, the retractable/expandable annular ring having a uni-flow mechanism may be used to replace a dysfunctional mitral valve, tricuspid valve, aortic valve, pulmonary valve or a venous valve.

The shape-memory material may be embedded within a biocompatible substrate selected from a group consisting of silicone, polyurethane, expanded polytetrafluoroethylene, semi-permeable material, biodegradable material, collagen, and mixture of the biocompatible substrate thereof, and the like. The embedding may make the annular ring impermeable to blood and provide supportive strength. Furthermore, an internal space of the fabric sheath may comprise a therapeutic agent selected from a group consisting of heparin agent, virucidal agent, anti-ulcer agent, anti-inflammatory agent, antibiotics, anti-cancer agent, and mixture of the therapeutic agent thereof. The therapeutic agent selected from a group consisting of heparin agent, virucidal agent, anti-ulcer agent, anti-inflammatory agent, antibiotics, anti-cancer agent, and mixture of the therapeutic agent thereof may be loaded onto the biocompatible substrate that embed the shape-memory material.

In another preferred embodiment, the shape-transition temperature for the shape-memory material is preferably between about 39° C. and about 90° C. The shape-transition temperature is further configured at a temperature region that is sufficient to cause the shape-memory material to transform to its preshape but not high enough to undesirably affect the tissues. In a medical implant comprising two shape-memory materials, each shape-memory material has its own shape-transition temperature. The source of heat for heating the shape-memory material to above the shape-transition temperature may be selected from a group consisting of radiofrequency energy, heated balloon, infrared energy, ultrasound energy, and laser energy. Alternately, the source of heat may comprise an external magnetic circuit or other remote source. If a shape-transition temperature is designed to be lower than the body temperature, then cryo source is used to trigger the shape change of the shape-memory material.

In one aspect, the fabric sheath may be stretchable or distensible to accommodate the distension of the annular ring at a later time. In a further embodiment, the fabric sheath may be impermeable to prevent blood from entering into the inner spaces. It may also comprise a silicone layer so that the annular ring is substantially impermeable to blood or blood components. The silicone layer may be placed between the fabric sheath and the inner circular members of the annular ring. The fabric sheath may be suturable to facilitate suturing-in-place of the ring to the surrounding anatomical tissue. The fabric sheath may be made of Dacron or other biocompatible material.

In accordance with another embodiment of the invention, the expandable annular ring for implantation in a heart valve annulus may comprise a fabric sheath and a plurality of stenting elements mounted within the fabric sheath, wherein each of the plurality of stenting elements is made of shape-memory material having a preshape and its own shape-transition temperature, wherein each shape-memory material expands to its preshape when that shape-memory material is heated to above its own shape-transition temperature. In an alternate embodiment, the fabric sheath may be eliminated from the annular ring structure or may be replaced by silicone or other suitable material for intended implantation purposes.

In still another embodiment, there is provided a method for radially expanding an expandable annular ring implanted in an annulus of a heart valve of a patient. The method may comprise the steps of implanting within the annulus an expandable annular ring having at least one stenting element made of shape-memory material. Subsequently, at an appropriate time, apply heat for radially expanding the annular ring to a size larger than the size at implantation, wherein the shape-memory material expands to its preshape when the shape-memory material is heated to above the shape-transition temperature. The same principle also applies to a shape-memory material having a shape-transition temperature lower than a body temperature that utilizes cooling means for triggering shape transition.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
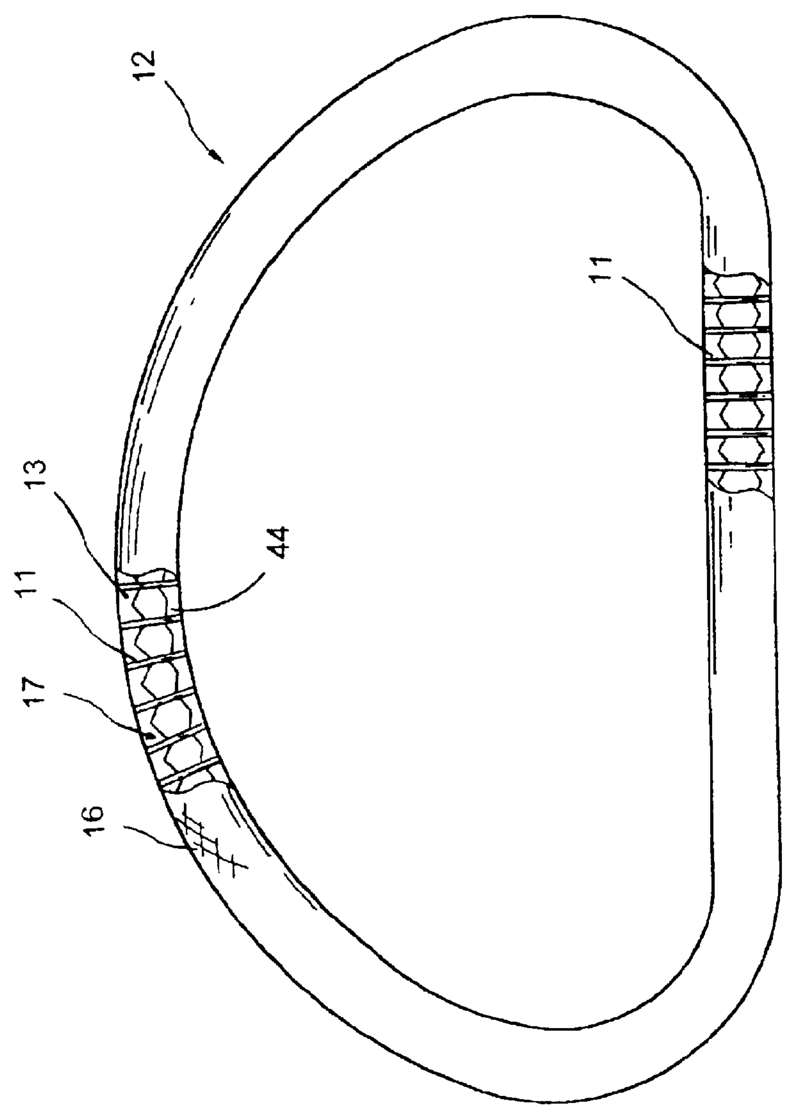
FIG. 1 is a partial perspective view of an embodiment of the expandable annular ring of the present invention.

With reference to the drawings FIGS. 1 to 8, what is shown is an embodiment of an expandable annular ring made of shape-memory materials having essentially uniform distensibility in the circumferential direction of the ring. The term "annular ring" is intended herein to mean any ring-shape structure suitable for placement at an annulus of a body. The term "annular ring with a uni-flow mechanism" is herein intended to mean any ring-shape structure incorporating a mechanism or structure for allowing fluid to flow through the annular ring in one direction, but not in an opposite direction. The uni-flow mechanism may comprise a plurality of valvular cusps configured for allowing fluid to flow through the annular ring in one direction.

It is one aspect of the present invention to provide an expandable annular ring with a uni-flow mechanism for implantation in a valvular annulus of a patient comprising a plurality of stenting elements evenly spaced along the annular ring, wherein the stenting elements are made of a shape-memory material, the shape-memory material having a preshape and a shape-transition temperature, wherein the shape-memory material expands to its preshape so as to expand the annular ring when the shape-memory material is heated to above the shape-transition temperature.

Jayaraman in U.S. Pat. No. 6,224,625, entire contents of which are incorporated herein by reference, discloses a low profile highly expandable stent including a Nitinol material. Jayaraman's stent is made of tubular pieces of material configured for the stent to expand both radially and longitudinally. Jayaraman further discloses a stent comprising generally cylindrical monolayer end pieces having a plurality of circumferentially spaced longitudinal slits showing a an intravascular/endoluminal stent that is significantly different from an annular ring in structure and in function of the present invention.

Further, Gabby in U.S. Pat. No. 4,491,986, entire contents of which are incorporated herein by reference, discloses a heart valve having a stenting element that constitutes a part of the valve, wherein the stenting element of the heart valve comprises a longitudinal portion to stabilize the valve leaflets. Nevertheless, Gabby does not disclose an expandable annular ring having two distinct sub-groups of stenting elements, wherein the stenting element is made of shape-memory material, the shape-memory material having a preshape and a shape-transition temperature, wherein one of the shape-memory material expands to its preshape so as to expand the annular ring when the shape-memory material is heated to above the shape-transition temperature.

Bessler et al. in U.S. Pat. No. 5,855,601, entire contents of which are incorporated herein by reference, discloses an artificial heart valve comprising a relatively rigid stent member, wherein the valve is retracted during delivery and expanded after deployment. The stent member may be self-expanding or change shape in response to temperature. The stenting elements are covered with by a sheath cuff portion. However, Bessler et al. does not disclose an expandable annular ring having a plurality of stenting elements, wherein the stenting element is made of shape-memory material, the shape-memory material having a preshape and a shape-transition temperature.

Tu et al. in U.S. Pat. No. 6,077,298, entire contents of which are incorporated herein by reference, discloses a retractable intraluminal medical device comprising an elongate radially expandable tubular stent made of shape-memory Nitinol having a retracted state for percutaneous insertion. The deployment of such a medical implant can be accomplished by a catheter-based percutaneous procedure while the expansion of the implant can be accomplished by triggering a shape transition of the shape-memory component of the implant, instead of by deploying an inflatable balloon. A delivery catheter and its mechanisms of stent deployment are well known to one who is skilled in the art. The expandable stent device may be made of a shape-memory coil, mesh, and the like.

Percutaneous Delivery Means

Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendinae, reattachment of severed atrioventricular valve chordae tendinae or papillary muscle tissue, and decalcification of valve and annulus tissue. Alternatively, the valve may be replaced, by excising the valve leaflets of the natural valve, and securing a replacement valve in the valve position, usually by suturing the replacement valve to the natural valve annulus.

A conventional procedure for approaching the left atrium is by intravascular catheterization from a femoral vein through the cardiac septal which separates the right atrium and the left atrium. It is also feasible to approach the left atrium by intravascular catheterization from a subclavian vessel. This intravascular procedure may be used for a percutaneous implantation of the annular ring and/or annular ring with a uni-flow mechanism of the present insertion.

Sterman et al. in U.S. Pat. No. 6,283,127, entire contents of which are incorporated herein by reference, discloses a device system and methods facilitating intervention within the heart or great vessels without the need for a median sternotomy or other form of gross thoracotomy, substantially reducing trauma, risk of complication, recovery time, and pain for the patient. Using the device systems and methods of the invention, surgical procedures may be performed through percutaneous penetrations within intercostal spaces of the patient's rib cage, without cutting, removing, or significantly displacing any of the patient's ribs or sternum. The device systems and methods are particularly well adapted for heart valve repair and replacement, facilitating visualization within the patient's thoracic cavity, repair or removal of the patient's natural valve, and, if necessary, attachment of a replacement valve in the natural valve position.

Of particular interest in the present application are techniques for the implantation of an annular ring with a uni-flow mechanism such as an atrioventricular valve that can be delivered to the valvular annulus location by a minimally invasive percutaneous procedure. In one aspect, the uni-flow mechanism comprises a plurality of valvular cusps configured for allowing fluid to flow through the annular ring in one direction. In one aspect, the annular ring with or without a uni-flow mechanism is retracted inside a delivery catheter system for percutaneous intravascular insertion. In another aspect, the annular ring with or without a uni-flow mechanism is retracted within a cannula for delivering through a less invasive intercostal penetration to the desired place, particularly in a left atrium. Thereafter the retracted annular ring is reversed to its preshape following the shape-memory principles. Further, a second deployment of the anchoring means for releasing a plurality of anchoring elements is adapted to secure the annular ring to the surrounding tissue with a minimally invasive technique, wherein the anchoring elements are made of shape-memory material.

Andersen et al. in U.S. Pat. No. 5,840,081, entire contents of which are incorporated herein by reference, discloses a system and method for implanting a cardiac valve by using a percutaneous catheter-based approach. Andersen et al. further discloses that the valve mounted to a collapsible stent is expanded by an expandable balloon. One drawback of balloon expanding mechanisms is the blood flow interruption which put a patient at an unnecessary high risk. An energy-initiated expanding mechanism on a shape-memory annular ring of the present invention does not interrupt blood flow. In some aspects, a guide-wire device or a catheter system having a conductive electrode at its distal section may be used for delivering radiofrequency energy to the shape-memory element enabling the shape-memory element to revert to its preshape.

The annular ring may comprise a silicone or fabric sheath to assist its positioning to engage the periphery of the annular ring with the inner wall of the valvular annulus. In a general aspect, the medical implant of the present invention comprises an annular ring with or without a uni-flow mechanism. It would also be desirable to provide a therapeutic agent selected from a group consisting of heparin agent, virucidal agent, anti-ulcer agent, anti-inflammatory agent, antibiotics, anti-cancer agent, and mixture of the therapeutic agent thereof to be loaded onto the silicone or fabric sheath that accompanying the shape-memory material of the annular ring.

Another aspect of the present invention is to fabricate an annular ring with a uni-flow mechanism and a delivery system thereof, wherein the uni-flow mechanism comprises a singular membrane of biocompatible material, such as a pericardium membrane that has at least two cusps configured to form a substantially tubular shape for use as a uni-flow valve. In a co-pending patent application Ser. No. 10/137,637 filed May 2, 2002, entire contents of which are incorporated herein by reference, discloses a supportless atrioventricular valve comprising a singular membrane of tissue. In one example, the annular ring with a uni-flow mechanism is an atrioventricular heart valve. The valve has an annular ring comprising an opening defined by a perimeter including at least a first and a second straight side portions thereof, an anterior cusp hinged continuously from the first straight side portion, a posterior cusp hinged continuously from the second straight side portion opposite the anterior cusp, wherein the anterior cusp and the posterior cusp are an integral part of a continuum from the singular membrane configured to form a substantially tubular shape for use as the atrioventricular valve. The posterior cusp and the anterior cusp are mounted onto an annular ring when the ring is in its preshape stage. The co-pending application also discloses a minimally invasive delivery system through a percutaneous intercostal penetration and a penetration at the cardiac wall to implant an annular ring with a uni-flow mechanism into a left atrium of the heart.

FIG. 1 shows a partial perspective view of a first embodiment of the expandable annular ring of the present invention. The annular ring 12 comprises a fabric sheath 16 and an annular ring element 17. In one embodiment, the annular ring element 17 comprises a plurality of circular members 11 mounted within the fabric sheath 16 and spaced from one another, wherein each of the plurality of circular members 11 is securely joined to an adjacent circular member by at least one stenting element 13 (and/or 44) so as to form a continuous annular ring element, wherein the at least one stenting element is made of shape-memory material. The shape-memory material may be selected from a group consisting of shape-memory Nitinol, shape-memory plastic, combination thereof, or other shape-memory substrate. The shape-memory material has a preshape and a shape-transition temperature, wherein the shape-memory material may be manipulated or constrained at will before an expansion state but expand to its preshape so as to expand circumferentially the annular ring when the shape-memory material is heated to above the associated shape-transition temperature.

The shape-memory material of the expandable annular ring with or without a uni-flow mechanism may be embedded within a biocompatible substrate selected from a group consisting of silicone, polyurethane, expanded polytetrafluoroethylene, semi-permeable material, biodegradable material, collagen, and mixture of the biocompatible substrate thereof or the like. For drug therapeutics purposes, the internal space within the annular ring or the substrate may be loaded with a therapeutic agent selected from a group consisting of heparin agent, virucidal agent, anti-ulcer agent, anti-inflammatory agent, antibiotics, anti-proliferative agent, anti-cancer agent, and mixture of the therapeutic agent thereof.

The therapeutic agent of the present invention may also comprise analgesics/antipyretics (e.g., aspirin), antiasthamatics (e.g., ketotifen), antibiotics (e.g., rapamycin), antidepressants (e.g., nefopam), antidiabetics (e.g., biguanides), antifungal agents (e.g., griseofulvin), antihypertensive agents (e.g., propanolol) anti-inflammatories (e.g., ibuprofen), antineoplastics (e.g., actinomycin), antianxiety agents (e.g., lorazepam), immunosuppressive agents (e.g., cyclosporine), antimigraine agents (e.g., ergotamine), sedatives/hypnotics (e.g., pentobarbital), antipsychotic agents (e.g., haloperidol), antimanic agents (e.g., lithium carbonate), antiarrhythmics (e.g., bretylium tosylate), antiarthritic agents (e.g., phenylbutazone), antigout agents (e.g., colchicine), anticoagulants (e.g., heparin), thrombolytic agents (e.g., urokinase), antifibrinolytic agents (e.g., aminocaproic acid), antiplatelet agents (e.g., aspirin), antibacterial agents (e.g., amikacin sulfate), antiviral agents (e.g., interferon alpha), antimicrobials (e.g., cefazolin sodium), and anti-infectives (e.g., GM-CSF).

The plurality of circular members 11 or partial circular members may be selected from the group consisting of Nitinol, Nickel-Titanium alloy, stainless steel, biocompatible metal, biocompatible plastic, and the like. The shape of the at least one of the plurality of circular members may be selected from the group consisting of a round shape, an oval shape, a C-shape, a D-shape, a U-shape, an open circular shape, and an irregular shape. The circular member may be relatively rigid or semi-flexible so as to support the valvular annulus during the heart valve functions of opening and closing. For one aspect of percutaneous insertion procedures, the circular member or partial circular member is configured and sized enabling for being retracted within a delivery cannula, sheath or catheter during the delivery stage.

The stenting elements 13, 44 are generally rigid and non-axially contractible so as to maintain the circumferential distance and the general shape of the annular ring. The stenting element may be distended axially (that is, in a circumferential direction when the stenting element is considered as a part of the whole annular ring element) by force or by returning to its preshape with additional energy and stays at the distended state upon distending. Frantzen in U.S. Pat. No. 6,042,606 discloses a radially expandable non-axially contracting surgical stent. By incorporating an extra tie-bar between any two wave-like struts of a conventional stent, axial contraction of the stent is avoided when the stent is radially expanded. The stenting element of the present invention may comprise a plurality of struts with tie-bars so as to maintain the circumferential integrity of the annular ring element. U.S. Pat. No. 6,042,606 is incorporated herein by reference.

The circular members (also including partial circular members throughout the specification) and their coupled stenting elements constitute the annular ring. As disclosed in a co-pending patent application Ser. No. 09/587,135, filed Jun. 2, 2000, when a dilatory or outward pressure is exerted against the inner surface of the annular ring introduced within the annulus, the stenting element may distend circumferentially while the annular ring expands radially. The stenting element may be selected from the group consisting of a mesh, a zigzag wire, a spiral wire, a stretchable stent, a spiral-like structure, and the like. In a preferred embodiment, the shape-memory stenting element is constrained or compressed in the original annular ring fabrication. It may be distended to its preshape by heating the stenting element above its shape-transition temperature.

Ehr et al. in U.S. Pat. No. 6,033,433 discloses a stent having spiral structures between expandable segments which absorbs excess stress when the expandable segments are expanded so as to avoid stent recoiling. The stenting element of the present invention may comprise a spiral structure or spiral wire to relieve the undesired local stress upon radial expansion of the annular ring. U.S. Pat. No. 6,033,433 is also incorporated herein by reference.

Figure 2A:
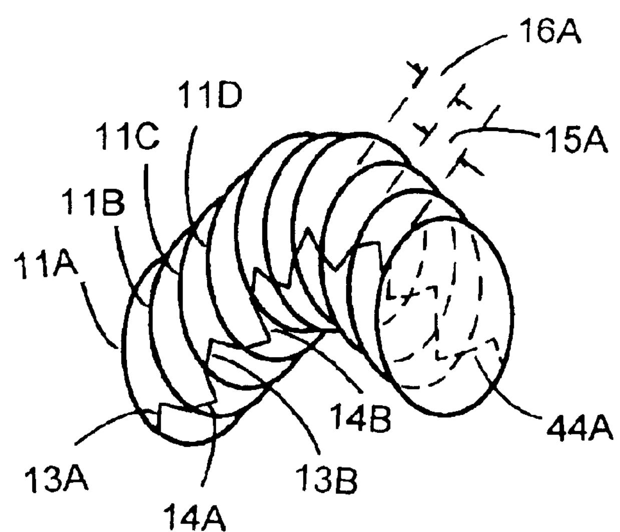
FIG. 2A is a perspective view of a plurality of stenting elements made of shape-memory material for the annular ring at a pre-expansion state.

FIG. 2A shows a perspective view of the plurality of circular members 11A, 11B, 11C, 11D and a plurality of stenting elements 13A, 13B, 14A, 14B made of shape-memory material at a pre-expansion or retracted (that is, compressed) state. For illustration purposes, at a pre-expansion state, a circular member 11A is securely joined to an adjacent circular member 11B by at least a stenting element 13A. Similarly, a circular member 11C is securely joined to an adjacent circular member 11D by at least another stenting element 14A.

In one preferred embodiment, the first set of stenting elements 13A, 13B is made of shape-memory material having a first shape-transition temperature which is different from that for the second set of stenting elements 14A, 14B, which have a second shape-transition temperature. The stenting elements of the present invention may comprise a plurality of sets, all having different shape-transition temperatures. Alternatively, at least one additional stenting element 44A may be used to securely join any two circular members at a location away from the prior joint point of a prior stenting element. The at least one additional stenting element, such as 44A may have the same or different shape-transition temperature as the corresponding stenting element for those two circular members.

Figure 5A:
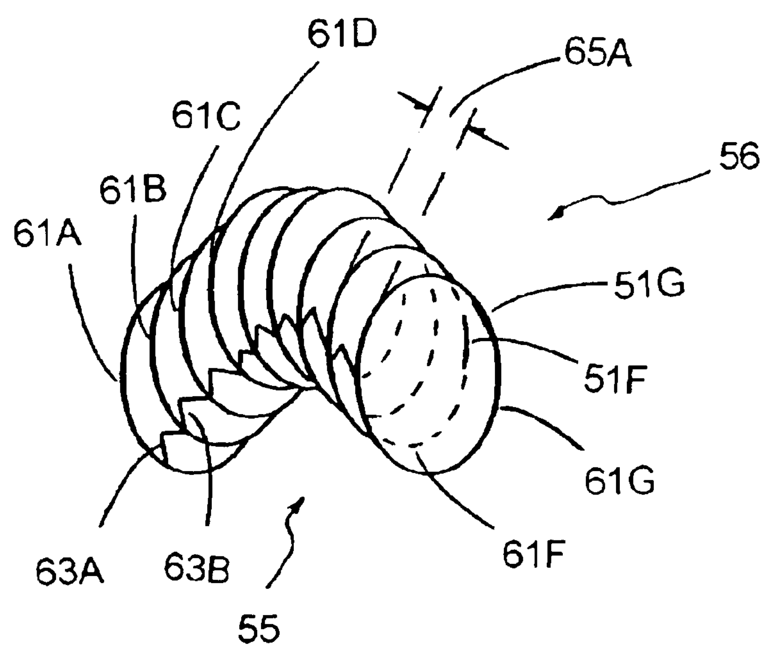
FIG. 5A is a perspective view of a preferred annular ring comprising two sub-groups of stenting elements made of shape-memory material for the annular ring at a pre-expansion state.

In another aspect of the present invention, the annular ring may comprise two or more sub-groups of circular or partial circular stenting members, wherein each sub-group has a plurality of stenting members supported by a plurality of stenting elements. In one embodiment as shown in FIG. 5A, a first sub-group comprises a plurality of circular members 61A, 61B, 61C, 61D and a plurality of stenting elements 63A, 63B made of shape-memory material at a pre-expansion or retracted state. The stenting elements 63A, 63B of the first sub-group have their shape-transition temperatures.

The annular ring of the present invention further comprises a second sub-group of stenting members (shown in FIG. 5A and FIG. 5B) that is coupled to an outer periphery of the corresponding circular members of the first sub-group. The second sub-group also comprises a plurality of shape-memory elements 51F, 51G made of shape-memory material at a pre-expansion or retracted state. The stenting elements 51F, 51G of the second sub-group have their shape-transition temperatures. For example, the shape-transition temperature for the first sub-group shape-memory material is preferably between about 39° C. and about 90° C. while the shape-transition temperature for the second sub-group shape-memory material is preferably between about 40° C. and about 90° C. The beat applied to the shape-transition Nitinol material is configured sufficient to cause shape change, but not to cause undesired tissue shrinkage or damage about the annual tissue.

The space or distance 15A between any two adjacent circular members in FIG. 2A and bridged by at least one stenting element 13A, or 13B of the first set of shape-memory material may be distended axially at above the first shape-transition temperature of that material. In an additional embodiment, the space or distance 16A between any two adjacent circular members and bridged by at least one stenting element 14A, or 14B of the second set of shape-memory material may be distended axially at above the second shape-transition temperature associated with the second set of shape-memory material.

Figure 2B:
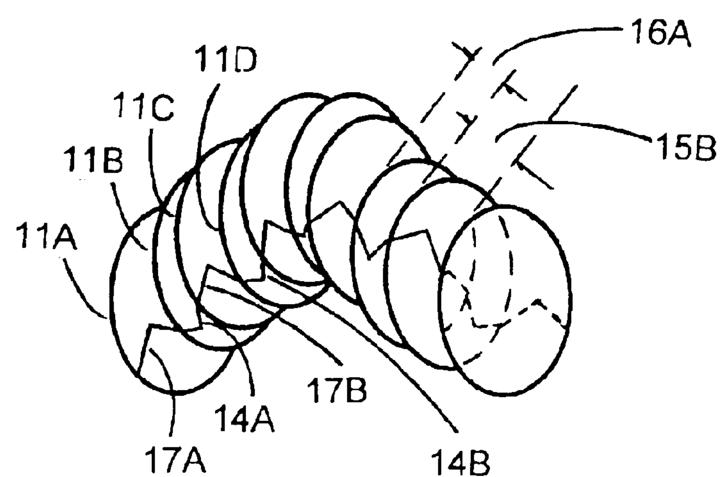
FIG. 2B is a perspective view of the corresponding plurality of stenting elements of FIG. 2A at a first post-expansion state.

FIG. 2B shows a perspective view of the corresponding plurality of stenting elements of FIG. 2A at a first post-expansion state by heating the stenting element above its first shape-transition temperature. The distended stenting elements 17A in reference to prior 13A (and/or 17B via 13B) as shown in FIG. 2B increase the distance between the two adjacent circular members of the first set shape-memory material from 15A to 15B. At this first post-expansion state, the stenting elements 14A, 14B made of the second set shape-memory material do not distend because the activating temperature is still below the second shape-transition temperature.

Figure 2C:
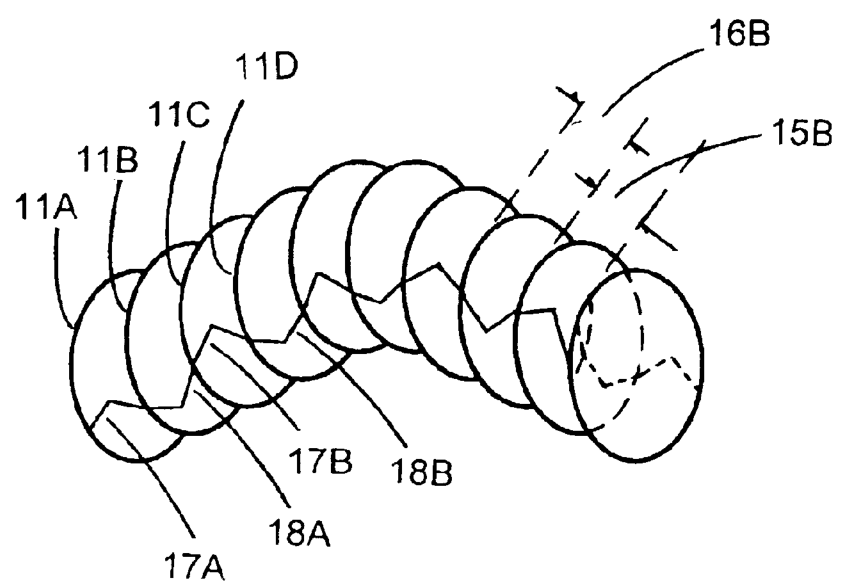
FIG. 2C is a perspective view of the corresponding plurality of stenting elements of FIG. 2A at a second post-expansion state.

FIG. 2C shows a perspective view of the corresponding plurality of stenting elements of FIG. 2A at a second post-expansion state by heating the stenting element above its second shape-transition temperature that is higher than the first shape-transition temperature. The distended stenting elements 18A in reference to prior 14A (and/or 18B via 14B) as shown in FIG. 2C increase the distance between the two adjacent circular members of the second set shape-memory material from 16A to 16B. At this second post-expansion state, the stenting elements 17A, 17B made of the first set shape-memory material do not distend any further because they are already at their preshape.

Figure 3B:
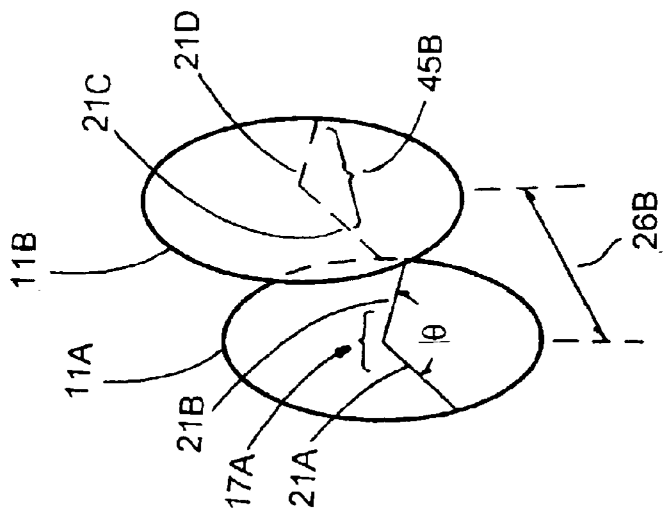
FIG. 3B is a schematic diagram illustrating one embodiment of the mechanisms for expanding the stenting elements made of memory-shape material axially outwardly at a post-expansion state leading to circumferential expansion of an annular ring.
Figure 3A:
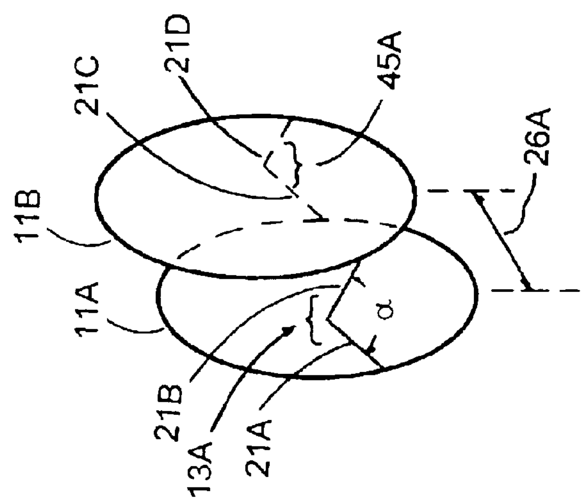
FIG. 3A is a schematic diagram illustrating one embodiment of the mechanisms for expanding the stenting elements made of memory-shape material axially outwardly at a pre-expansion state.

FIG. 3A and FIG. 3B show schematic diagrams illustrating one embodiment of the mechanisms for expanding the stenting element 13A made of memory-shape material axially outwardly leading to circumferential expansion of an annular ring. The two adjacent circular rings 11A, 11B or partial circular rings may be essentially parallel to each other. The distance between these two adjacent circular members 11A, 11B at a pre-expansion state is designated as 26A, while the two circular members may be joined by one stenting element 13A or at least one more stenting element 45A. In one illustrative embodiment, the stenting element 13A comprises two joint bars 21A and 21B that have been constrained at an angle $\alpha$ at a pre-expansion state. Similarly, the stenting element 45A comprises two joint bars 21C and 21D that have been constrained at a pre-expansion state. The purpose of the stenting elements is to support the circular member 11A, 11B in essentially perpendicular to a circumferential reference line of the annular ring. Another purpose of the stenting elements is to maintain the distance between the two adjacent circular members either at a pre-expansion state (that is, pre-distending state), or at a post-expansion state (that is, post-distending state).

Upon one expansion process by applying the expanding means of the present invention at a temperature above its first shape-transition temperature, the stenting elements 13A, 45A in FIG. 3A may be distended/stretched to become as 17A and 45B, respectively as shown in FIG. 3B. The distance between the two adjacent circular members 11A and 11B may increase from 26A to 26B after a first expansion and maintain the distended distance. At a first expansion state, the stenting element 17A comprising two joint bars 21A and 21B becomes conformed to its preshape at an angle $\theta$. Upon an optional second expansion process at a temperature above the second shape-transition temperature, the stenting elements made of second set shape-memory material may distend to their preshape. Therefore in one aspect, it is understandable that the total circumference of the annular ring may be adjusted more than once when there is more than one set of shape-memory stenting elements. The distending process and mechanism for maintaining a stent-like structure at the distended state as applied to the stenting element of the present invention is well known to one artisan who is skilled in the art.

Figure 4:
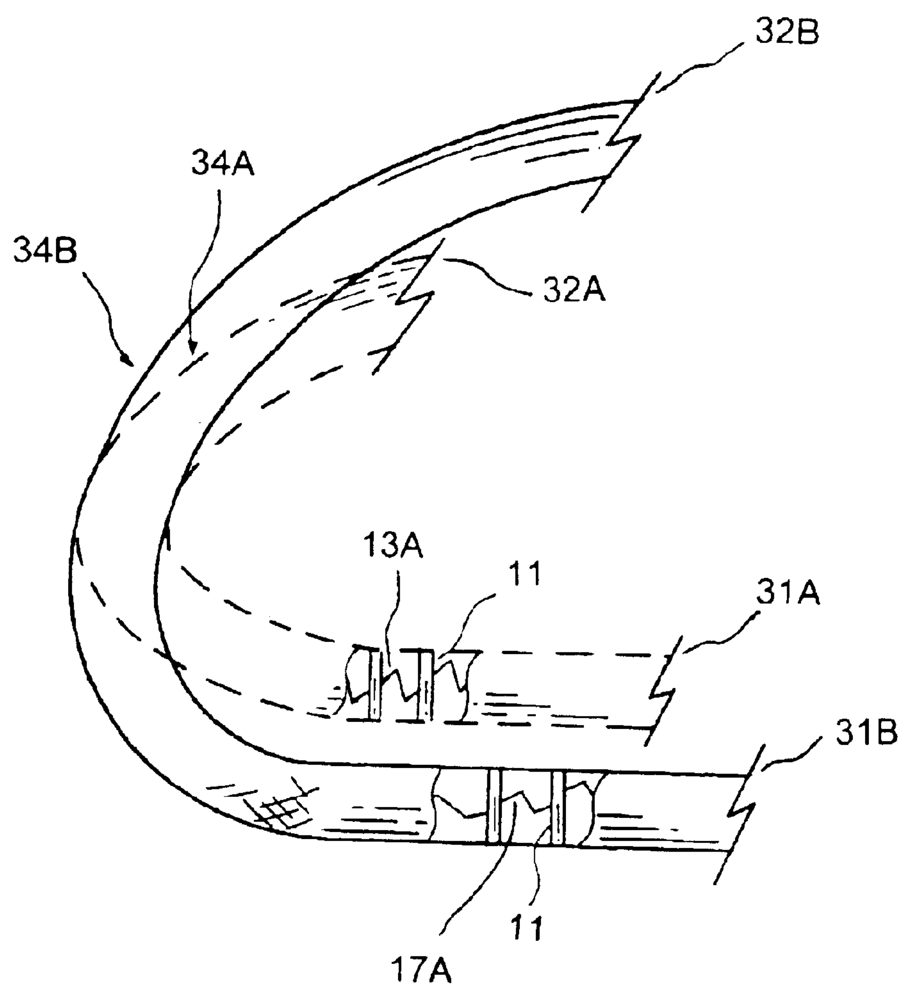
FIG. 4 is a cut-away illustration of an annular ring before and after circumferential expansion.

FIG. 4 shows a cut-away illustration of an annular ring before and after a radial expansion, that is, circumferential stretching. A first reference point 31A of a pre-expansion annular ring 34A becomes the reference point 31B for a first post-expansion annular ring 34B. A second reference point 32A from a pre-expansion annular ring 34A becomes the second reference point 32B for a first post-expansion annular ring 34B. Similarly, one of the at least one stenting element 13A between two adjacent circular rings 11 has been extended to become 17A at a post-expansion state.

FIG. 5A shows a perspective view of a preferred annular ring of the present invention comprising two sub-groups of stenting elements made of shape-memory material for the annular ring at a pre-expansion state. The annular ring comprises a plurality of supporting circular or partial circular members 61A, 61B, 61C, 61F, 61G and a plurality of first sub-group stenting elements 63A, 63B made of shape-memory material at a pre-expansion or retracted state adapted for suitable percutaneous insertion.

The annular ring further comprises a second sub-group anchoring element 51F, 51G with one end secured to each supporting member 61F, 61G, respectively. For illustration purposes in one aspect, at a pre-expansion state, a circular member 61A is securely joined to an adjacent circular member 61B by at least a stenting element 63A. Similarly, a circular member 61B is securely joined to an adjacent circular member 61C by at least another stenting element 63B. In one preferred embodiment, the first sub-group of stenting elements 63A, 63B is made of shape-memory material having a first shape-transition temperature which is different from that for the second sub-group of anchoring elements 51F, 51G, which have a second shape-transition temperature.

Bessler et al. in U.S. Pat. No. 5,855,601, entire contents of which are incorporated herein by reference, discloses an artificial heart valve having a plurality of barbs for holding the valve in place once the valve has been appropriately positioned. However, Bessler et al. teaches only a passive barb-holding characteristics for an artificial heart valve, but not an active anchoring mechanism by shape-memory anchoring elements that are triggered at an appropriate time when the annular ring with a uni-flow mechanism of the present invention is ready for final positioning.

Figure 5B:
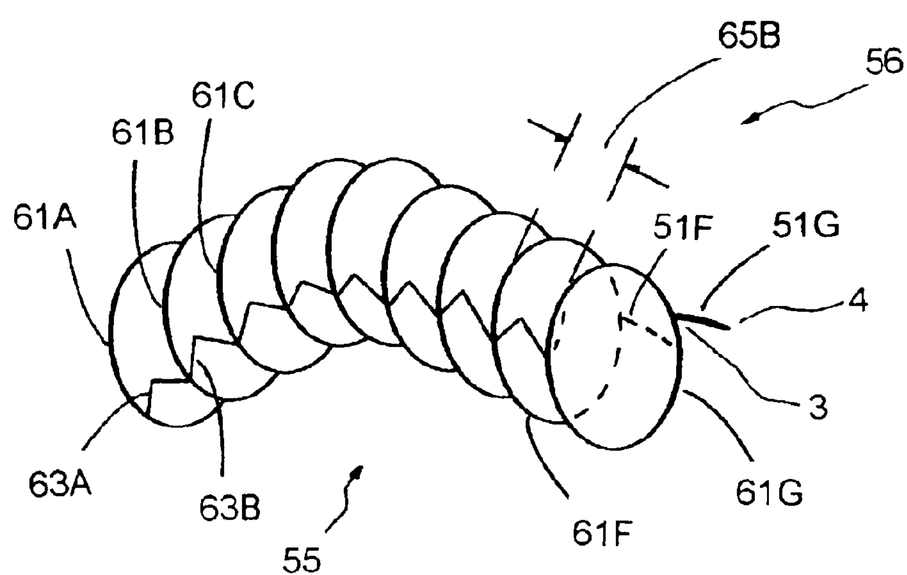
FIG. 5B is a perspective view of the corresponding stenting elements of FIG. 5A at a post-expansion anchoring state.

FIG. 5B shows a perspective view of the corresponding stenting elements of FIG. 5A at a post-expansion anchoring state. An annular ring in its retracted state as shown in FIG. 5A is inserted percutaneously through a vascular opening or through an intercostal opening to the location of a heart valve to be replaced or repaired. Once the annular ring is placed about the target location, the annular ring is radially expanded by heating the stenting elements of the first sub-group above its first shape-transition temperature. The distended stenting elements increase the distance between the two adjacent circular members of the first sub-group shape-memory material from 65A to 65B. At this first post-expansion state, the anchoring elements 51F, 51G (also known as the second stenting elements) made of the second sub-group shape-memory material do not change shape because the activating temperature is still below the second shape-transition temperature.

In some aspects for illustration, each of anchoring elements 51G of the second sub-group is configured to have a proximal end 3 and a distal end 4, wherein the proximal end 3 is secured to its corresponding circular ring 61G while the distal end 4 is free to swing outwardly. During the implant insertion stage, the anchoring element 51F or 51G is configured and sized enabling the distal end 4 of the swingable element 51F intimately placed along the circular member 61F without obstructing the annular ring delivery. After the annular ring is expanded and is ready for anchoring into the surrounding annulus tissue, the anchoring elements 51F, 51G are activated by heating the elements 51F, 51G of the second sub-group above its second shape-transition temperature. The sharp distal ends of the activated elements 51F, 51G point radially outwardly to penetrate into the annulus tissue. As shown in FIG. 5A and FIG. 5B, the activated elements 51F, 51G are generally facing the exterior side 56 of the annular ring and are away from the interior side 55 of the ring.

One method by which the size of the annular ring may be expanded is through introduction of heat to the shape-memory stenting element to above its shape-transition temperature so as to convert the constrained or retracted configuration to its preshape configuration. The source of heat may be selected from a group consisting of radiofrequency (RF) energy, heated balloon, infrared (IR) energy, ultrasound energy, and laser energy. The heat is generally introduced to the stenting element through a catheter, a wire, a guide wire, a conducting wire, fiber optics, or other appropriate means. In one embodiment of the present invention, the stenting elements may be electrically connected to each other so as to transfer the heat or energy through all or part of the stenting elements of the annular ring or the annular ring with a uni-flow mechanism.

In an alternate embodiment, the source of heat may comprise an external magnetic circuit, whereby heating of the shape-memory stenting element is induced based on when being placed into an alternative magnetic field. Accordingly, magnetic flux rapid alteration results in power loss to the magnetic circuit that appears as heat on the stenting element in vivo. Other non-invasive methods for heating the shape-memory stenting elements of the present invention may be applicable that are covered in the disclosure.

Figure 6:
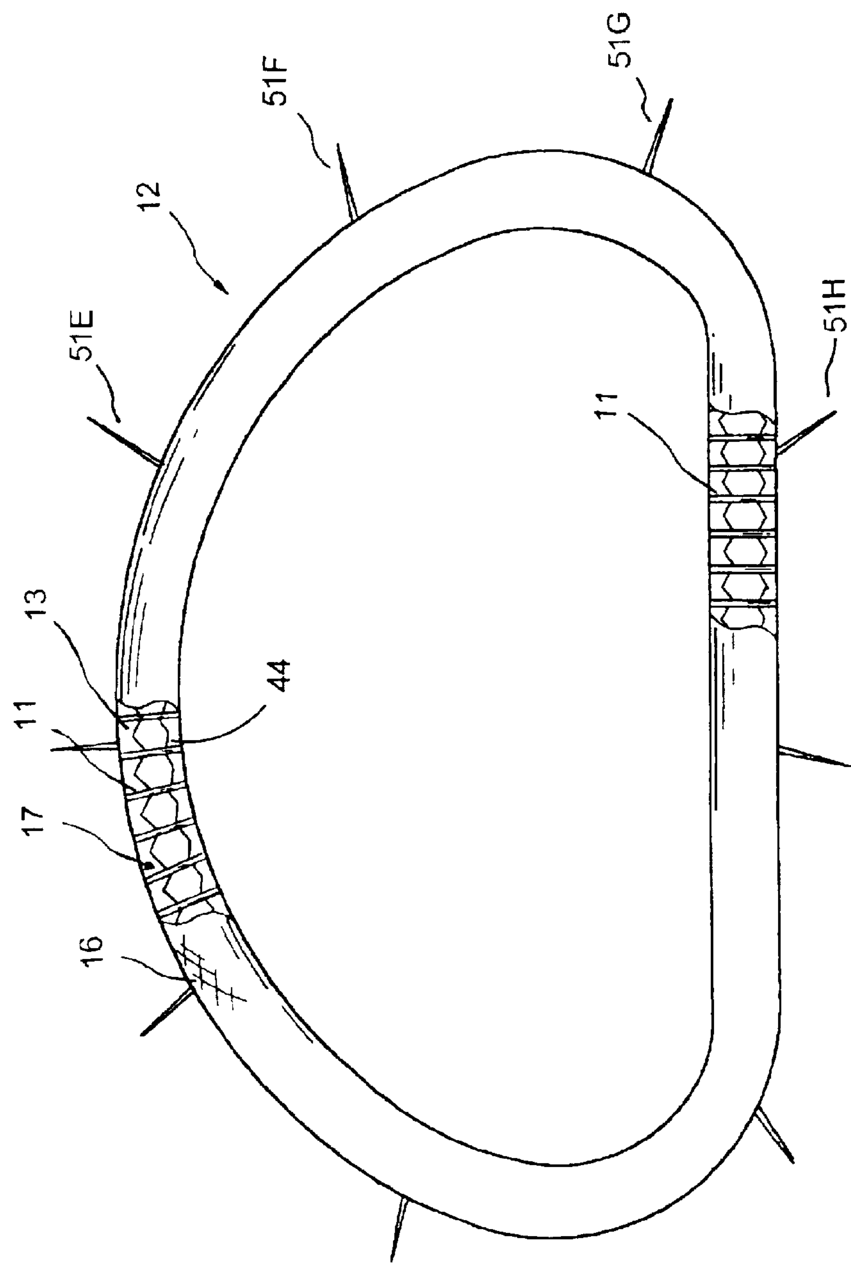
FIG. 6 is an aspect of an annular ring having a stenting element made of a first memory-shape material and an anchoring element made of a second memory-shape material.

FIG. 6 shows an aspect of an expandable annular ring for implantation in a valvular annulus comprising: a plurality of stenting elements made of a first shape-memory material having a first preshape and a first shape-transition temperature, wherein the first shape-memory material expands to the first preshape when the first shape-memory material is heated to above the first shape-transition temperature; and a plurality of anchoring elements made of a second shape-memory material having a second preshape and a second shape-transition temperature that is higher than the first shape-transition temperature, wherein the second shape-memory material expands to the second preshape when the second shape-memory material is heated to above the second shape-transition temperature. Each anchoring element comprises a distal end and a proximal end, wherein the proximal ends of the anchoring elements are secured at a periphery of the annular ring configured for enabling the distal ends of the anchoring elements positioning in a radially outward direction when the second shape-memory material is heated to above the second shape-transition temperature. At an expanded anchoring stage, all the anchoring elements 51E, 51F, 51G, 51H and so forth facing essentially the surrounding annulus tissue direction sufficient for anchoring the annular ring snugly into the annulus tissue in place.

In an illustrative embodiment, a method for radially expanding an expandable annular ring implanted in an annulus of a heart valve of a patient, the method comprising steps of implanting within the annulus an expandable annular ring having at least one stenting element by either an open-heart surgery or by percutaneous insertion means, wherein the at least one stenting element is made of shape-memory material, the shape-memory material having a preshape and a shape-transition temperature. And subsequently, after the annular ring is in place or after a predetermined time duration, applying heat for radially expanding the annular ring to a size larger than the size at first insertion, wherein the shape-memory material expands to its preshape when the shape-memory material is heated to above the shape-transition temperature.

It is a further aspect of the present invention to provide a method for implanting an expandable annular ring having a plurality of stenting elements made of a first shape-memory material with a first shape-transition temperature and a plurality of anchoring elements made of a second shape-memory material with a second shape-transition temperature that is higher than the first shape-transition temperature in a valvular annulus of a patient, the method comprising steps of: (a) delivering the annular ring to the valvular annulus; (b) expanding the annular ring to intimately contact an inner wall of the valvular annulus by heating the first shape-memory material above the first shape-transition temperature; and (c) deploying the anchoring elements to penetrate into a surrounding annulus tissue by heating the second shape-memory material above the second shape-transition temperature.

The annular ring may further comprise a uni-flow mechanism configured to allow fluid to flow through the annular ring in one direction only. In one aspect of the present invention, the uni-flow mechanism is a check valve that allows fluid to flow in one direction, but not in an opposite direction. In another aspect, a natural heart valve or venous valve is one kind of the uni-flow mechanisms referred herein. Therefore, the annular ring with a uni-flow mechanism of the present invention may comprise a bioprosthetic heart valve or a venous valve for valve replacement.

Figure 7:
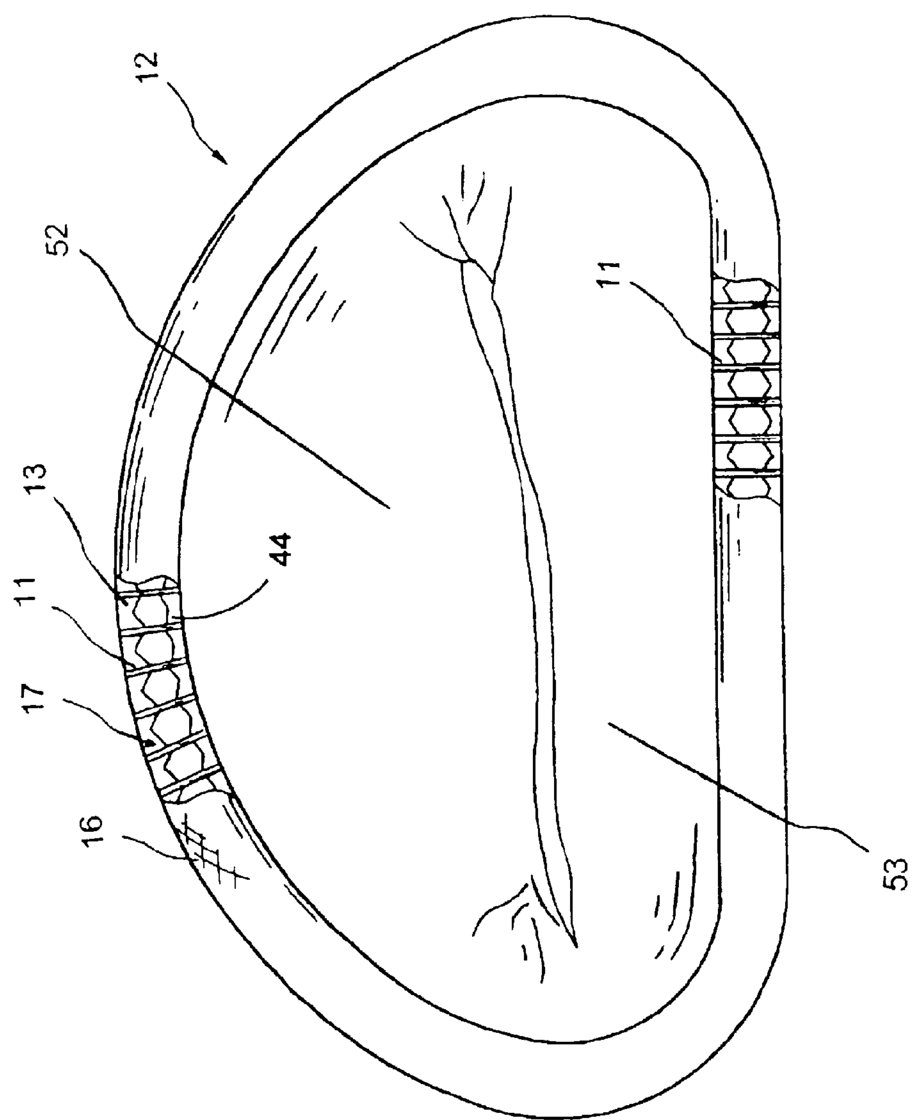
FIG. 7 is a top view of an annular ring having a uni-flow mechanism.

FIG. 7 shows a top view of an annular ring having a uni-flow mechanism. In some aspects of the present invention, a plurality of cusps 52, 53 are incorporated to the annular ring.

Figure 8A:
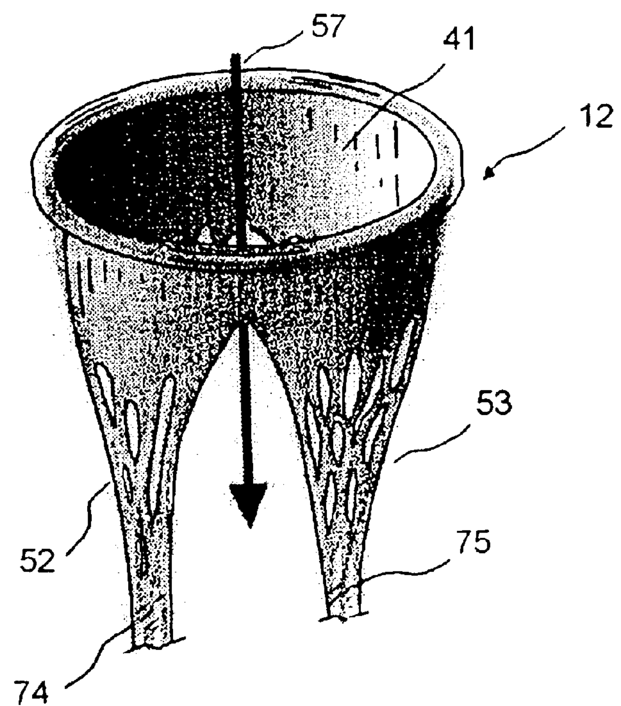
FIG. 8A is a perspective view of an annular ring with a uni-flow mechanism following the fluid flow direction.
Figure 8B:
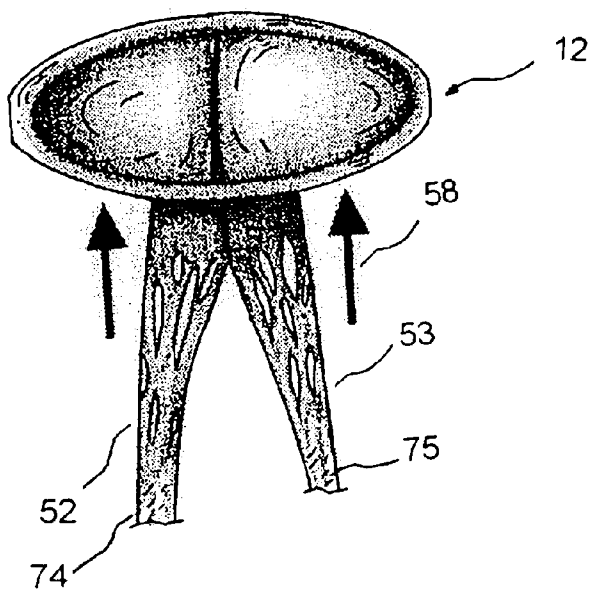
FIG. 8B is a perspective view of an annular ring with a uni-flow mechanism against the fluid flow direction.

FIG. 8A shows a perspective view of an atrioventricular valve (an annular ring with a uni-flow mechanism of FIG. 7) following the blood flow direction (that is, the valve is open), while FIG. 8B shows a perspective view of an atrioventricular valve against the blood flow direction (that is, the valve is closed). During an atrial relaxation phase, the atrioventricular valve cusps are open toward to the ventricle cavity along with the blood flow direction (arrow 57). During a ventricular contraction phase, the atrioventricular cusps tend to push back against the blood flow direction (arrow 58). The atrioventricular valve according to the present invention may also be flexible and retractable/foldable within a delivery apparatus for minimally invasive delivery purposes.

The co-pending application Ser. No. 10/137,637 filed May 2, 2002 by the co-inventors of this application discloses an illustrative atrioventricular valve having a annular ring 12 comprising an opening 41 defined by a perimeter including at least a first and a second straight side portions thereof, an anterior cusp 52 hinged continuously from the first straight side portion, a posterior cusp 53 hinged continuously from the second straight side portion opposite the anterior cusp, wherein the anterior cusp and the posterior cusp are an integral part of a continuum from the singular membrane configured to form a substantially tubular shape for use as the atrioventricular valve. Further, the anterior cusp 52 and the posterior cusp 53 further comprise texture elements 74, 75 at edge portions of the cusps 52, 53 configured to extend the texture elements for connection to papillary muscles in a ventricle cavity when the annular ring 12 is secured by anchoring elements to an atrioventricular junction of a patient heart.

In a minimally invasive procedure, a method for percutaneously delivering an atrioventricular valve for treating a leaky valve may comprise the steps of: (1) delivering the atrioventricular valve at a retracted state to the anatomical valvular position percutaneously during a delivery phase; (2) deploying the atrioventricular valve during a deployment phase; (3) expanding the atrioventricular valve at about the anatomical valvular annulus by applying a first shape-transition energy to activate the stenting elements so as to revert the retracted valve to its preshape; and (4) applying a second shape-transition energy to activate the anchoring elements for securing the valve into the annulus tissue. The method may further comprise forming a plurality of percutaneous intercostal penetrations in a patient's chest, each of the percutaneous intercostal penetrations being within an intercostal space between two adjacent ribs, wherein the atrioventricular valve is delivered through one of the percutaneous intercostal penetrations.

From the foregoing description, it should now be appreciated that a radially expandable annular ring or an annular ring with a uni-flow mechanism having essentially uniform ring distension in the circumferential direction has been disclosed for implantation in a heart valve annulus. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. An expandable ring with a uni-flow mechanism for implantation in a valvular annulus of a patient comprising a plurality of stenting elements evenly spaced along said annular ring, wherein said stenting elements are made of a shape-memory material, the shape-memory material having a preshape and a shape-transition temperature, wherein the shape-memory material expands to its preshape so as to expand the annular ring when said shape-memory material is heated to above the shape-transition temperature;

said ring having a plurality of circular members.

2. The expandable ring with a urn-flow mechanism according to claim 1, wherein said shape-memory material is selected from a group consisting of shape-memory Nitinol, shape-memory plastic, and combination thereof.

3. The expandable ring with a urn-flow mechanism according to claim 1, wherein said uni-flow mechanism comprises a plurality of valvular cusps configured for allowing fluid to flow through the annular ring in one direction.

4. The expandable ring with a urn-flow mechanism according to claim 1, wherein the shape-transition temperature for said shape-memory material is between about 39° C. and about 90° C.

5. An expandable ring for implantation in a valvular annulus comprising: a plurality of stenting elements made of a first shape-memory material having a first preshape and a first shape-transition temperature, wherein the first shape-memory material expands to the first preshape when said first shape-memory material is heated to above the first shape-transition temperature; and a plurality of anchoring elements made of a second shape-memory material having a second preshape and a second shape-transition temperature that is higher than the first shape-transition temperature, wherein the second shape-memory material expands to the second preshape when said second shape-memory material is heated to above the second shape-transition temperature.

6. The expandable ring according to claim 5, wherein said first and second shape-memory materials are selected from a group consisting of shape-memory Nitinol, shape-memory plastic, and combination thereof.

7. The expandable ring according to claim 5 further comprising a uni-flow mechanism for allowing fluid to flow through said a ring in one direction.

8. The expandable ring according to claim 5, wherein said plurality of stenting elements are evenly spaced along said ring configured for enabling essentially uniform ring distension in a circumferential direction when said first shape-memory material is heated to above the first shape-transition temperature.

9. The expandable ring according to claim 5, wherein the first shape-transition temperature is between about 39° C. and about 90° C.

10. The expandable ring according to claim 5, each anchoring element comprising a distal end and a proximal end, wherein the proximal ends of said anchoring elements are secured at an periphery of the ring configured for enabling the distal ends of said anchoring elements positioning in a radially outward direction when said second shape-memory material is heated to above the second shape-transition temperature.

11. The expandable ring according to claim 5, wherein the second shape-transition temperature is between about 40° C. and about 90° C.

12. The expandable ring according to claims 5 or 7 wherein said first shape-memory material is embedded within a biocompatible substrate selected from a group consisting of silicone, polyurethane, expanded polytetrafluoroethylene, semi-permeable material, biodegradable material, collagen, and mixture of said biocompatible substrate thereof.

13. The expandable ring according to claim 12 further comprising a therapeutic agent loaded within said biocompatible substrate.

14. The expandable ring according to claim 13, wherein the therapeutic agent is heparin.

15. The expandable ring according to claim 13, wherein the therapeutic agent is an anti-inflammatory agent.

16. The expandable ring according to claim 13, wherein the therapeutic agent is an antibiotics.

17. The expandable ring according to claim 13, wherein the therapeutic agent is an anti-proliferative agent.

18. A method for implanting an expandable ring having a plurality of stenting elements made of a first shape-memory material with a first shape-transition temperature and a plurality of anchoring elements made of a second shape-memory material with a second shape-transition temperature that is higher than the first shape-transition temperature in a valvular annulus of a patient, the method comprising steps of: (a) delivering said ring to the valvular annulus; (b) expanding said ring to intimately contact an inner wall of the valvular annulus by heating the first shape-memory material above the first shape-transition temperature; and (c) deploying the anchoring elements to penetrate into a surrounding annulus tissue by heating the second shape-memory material above the second shape-transition temperature.

19. The method according to claim 18, wherein the ring further comprises a urn-flow mechanism that allows fluid to flow through said ring in one direction.

20. The method according to claim 18, wherein the step for delivering said ring to the valvular annulus is through a percutaneous opening of the patient.

* * * * *

UNITED STATES PATENT AND TRADEMARK OFFICE

CERTIFICATE OF CORRECTION

PATENT NO. : 6,805,711 B2
DATED : October 19, 2004
INVENTOR(S) : Rodolfo C. Quijano and Hosheng Tu It is certified that error appears in the above-identified patent and that said Letters Patent is hereby corrected as shown below:

Column 16,
Lines 3 and 7, "urn-flow" should be changed to -- uni-flow --

Signed and Sealed this

Twenty-fourth Day of May, 2005

JON W. DUDAS
*Director of the United States Patent and Trademark Office*